(12) United States Patent
Sichau et al.

(10) Patent No.: US 9,839,479 B2
(45) Date of Patent: Dec. 12, 2017

(54) MEDICAL WASTE CONTAINMENT DEVICE

(71) Applicants: Gary S. Sichau, Chelmsford, MA (US); Terence K. Gray, Burlington, CT (US)

(72) Inventors: Gary S. Sichau, Chelmsford, MA (US); Terence K. Gray, Burlington, CT (US)

(*) Notice: Subject to any disclaimer, the term of this patent is extended or adjusted under 35 U.S.C. 154(b) by 1202 days.

(21) Appl. No.: 13/986,138

(22) Filed: Apr. 4, 2013

(65) Prior Publication Data

US 2013/0306507 A1 Nov. 21, 2013

Related U.S. Application Data

(60) Provisional application No. 61/686,371, filed on Apr. 4, 2012.

(51) Int. Cl.
| | | |
|---|---|---|
| *A61B 19/02* | (2006.01) | |
| *A61B 50/39* | (2016.01) | |
| *A61B 50/36* | (2016.01) | |
| *A61B 50/00* | (2016.01) | |
| *A61B 50/30* | (2016.01) | |

(52) U.S. Cl.
CPC .......... *A61B 19/0288* (2013.01); *A61B 50/36* (2016.02); *A61B 50/362* (2016.02); *A61B 50/39* (2016.02); *A61B 2050/0056* (2016.02); *A61B 2050/3008* (2016.02)

(58) Field of Classification Search
CPC ... A61B 19/0288; A61B 50/36; A61B 50/362; A61B 50/37; A61B 50/39; A61B 2050/0056; A61B 2050/006; A61B 2050/105; A61B 2050/3008; B65D 25/005; B65D 25/101; B65D 50/045; B65D 2251/1016

USPC .............. 206/210, 363–366, 370; 220/523, 220/908–909; 588/249
See application file for complete search history.

(56) References Cited

U.S. PATENT DOCUMENTS

| | | | | |
|---|---|---|---|---|
| 5,172,808 A | * | 12/1992 | Bruno ................. | A61M 5/3205 206/364 |
| 5,372,252 A | * | 12/1994 | Alexander ............ | A61M 5/001 206/210 |
| 5,385,105 A | * | 1/1995 | Withers, Jr. ........ | A61M 5/3205 206/371 |
| 5,495,941 A | * | 3/1996 | Leonard ................. | A61B 50/36 206/366 |
| 5,584,386 A | * | 12/1996 | Ahonen .................... | A61L 2/26 206/210 |

(Continued)

*Primary Examiner* — J. Gregory Pickett
*Assistant Examiner* — Brijesh V. Patel

(57) ABSTRACT

A device that stores, secures, and disinfects hazardous materials introduced therein, comprising a container having at least one interior surface, wherein the at least one interior surface forms at least one chamber within the container for storing the hazardous materials introduced into the container; at least one port having an aperture and unidirectional access for introducing the hazardous materials into the container and preventing outflow of the hazardous materials from the container; an absorbent material for securing the hazardous materials introduced into the container, wherein the absorbent material is affixed to the at least one interior surface of the container; and a disinfecting substance for disinfecting the hazardous materials introduced into the container, wherein the disinfecting substance is affixed to the at least one first interior surface of the container.

19 Claims, 12 Drawing Sheets

(56) References Cited

U.S. PATENT DOCUMENTS

| | | | | |
|---|---|---|---|---|
| 6,123,188 A | * | 9/2000 | Ahonen | A61L 2/18 |
| | | | | 206/210 |
| 8,096,414 B2 | * | 1/2012 | Finnestad | A61B 50/362 |
| | | | | 206/216 |
| 2009/0100661 A1 | * | 4/2009 | Panek, Jr. | A61M 5/3205 |
| | | | | 29/426.1 |
| 2009/0294312 A1 | * | 12/2009 | Hitson | B65F 1/10 |
| | | | | 206/364 |
| 2011/0297567 A1 | * | 12/2011 | Maness | A61M 5/3205 |
| | | | | 206/366 |

* cited by examiner

MEDICAL WASTE CONTAINMENT DEVICE

RELATED APPLICATION

This application claims the benefit of U.S. provisional patent application No. 61/686,371 filed Apr. 4, 2012, the contents of which are incorporated by reference in their entirety.

FIELD OF THE INVENTION

The subject invention relates to devices used in the medical field. Specifically, the invention relates to medical waste containment and disinfecting systems.

BACKGROUND OF THE INVENTION

In the medical field, it is common that excess fluids in the form of drugs or vaccines are drawn from vials and must afterward be safely and securely disposed of along with the syringe into which it was drawn. Fluids drawn from the human body must also be safely and securely disposed of, as well as the needles and syringes used to draw those fluids. In addition to the needles, syringes, and fluids previously mentioned, medical instruments which have been contaminated are commonly discarded and must be disposed of safely and securely to prevent spillage, exposure to environments where contamination can spread, or contact with skin or clothing.

Currently many federal, state and local agencies and organizations have placed restrictions on how and where many liquid preparations must be stored and discarded. Prior to the events that brought about these regulations and restrictions, such liquids were often disposed of in normal trash holders or simply placed down sinks, toilets and drains where these liquids would then find their way into our ecosystem. Various compounds and their substrates were commonly being discovered in both ground water supplies and in landfills.

In an effort to stop this contamination, restrictions have been placed on how and where many fluids must be deposited and stored for proper disposal. Despite regulations as to how fluids should be disposed of, there have been no satisfactory solutions as to how this can be done safely, effectively and securely.

BRIEF SUMMARY

It is therefore an object of this invention to provide a new and secure medical waste containment system and method used to safely introduce, store, secure, and disinfect contaminated, hazardous or biohazardous materials.

It is a further object of this invention to provide such a system to securely store hazardous materials in separate chambers within the system, depending upon whether the hazardous materials are a fluid, gas or medical instrument or device.

It is a further object of this invention to provide such a system to securely introduce hazardous materials into the system, and to prevent the outflow of the hazardous materials from the system, once the hazardous materials are introduced.

It is a further object of this invention to provide such a system and method which operates to measure and indicate the internal pressure of the system.

It is a further object of this invention to provide such a system and method which operates to release and disinfect excess pressure within the system.

It is a further object of this invention to provide such a system and method which operates to measure and indicate the saturation level of absorbent materials within the system.

It is a further object of this invention to provide such a system and method which operates to measure and indicate the toxicity of the absorbent material within the system.

It is a further object of this invention to provide such a system to attach multiple systems together to form a single convenient separable system.

It is a further object of this invention to provide such a system to allow for the incineration of the hazardous materials without opening or unsealing the container.

It is a further object of this invention to provide such a system and method which operates to distinguish the contents of the system by color or other visual indicators.

In accordance with an aspect of the inventive concepts, the improved medical waste containment device can be used to safely introduce, store, secure and disinfect contaminated, hazardous, or biohazardous fluids, gases or solids, hereinafter referred to as hazardous materials, introduced into or produced in the container, where the device comprises a container, having at least one interior surface, wherein the at least one interior surface join to form at least one chamber within the container, for storing the hazardous materials introduced into the container; at least one port, having an aperture and unidirectional access, for introducing the hazardous materials into the container and preventing outflow of the hazardous materials from the container; an absorbent material, for securing the hazardous materials introduced into the container, wherein the absorbent material is affixed to the at least one interior surface of the container; and a disinfecting substance, for disinfecting the hazardous materials introduced into the container, wherein the disinfecting substance is affixed to the at least one interior surface of the container.

In another embodiment, the absorbent material is combined with the disinfecting substance to secure and disinfect hazardous materials introduced into the container, wherein the combined absorbing material and disinfecting substance is affixed to the at least one interior surface of the container.

In another embodiment, an absorbent mesh layer having disinfecting properties is affixed to the at least one interior surface of the container to absorb and disinfect the hazardous materials introduced into the container.

In another embodiment, the at least one chamber of the container is divided into at least a first chamber and a second chamber to separately store the hazardous materials, and the first chamber and the second chamber are separated by a non-permeable partition, wherein the absorbent material is affixed to the at least one interior surface of the first chamber, second chamber and non-permeable partition.

In another embodiment, a third chamber is separated from at least the first chamber by a permeable partition, wherein the permeable partition can allow hazardous materials introduced into at least the first chamber to pass at least partially through to at least the third chamber.

In another embodiment, at least the first chamber is enclosed and completely separated from at least the second chamber and includes the at least one port which can be exclusive to the first chamber to introduce the hazardous materials exclusively into the first chamber.

In another embodiment, the at least one port includes a first aperture entirely enclosed by a first barrier, having at least one elastic layer, through which a needle attached to a syringe is inserted to introduce the hazardous materials into the container, whereby the first barrier prevents outflow of the hazardous materials from the container once the needle is removed from the first aperture.

In another embodiment, the at least one port includes a second aperture, to introduce the hazardous materials into the container, where the second aperture is entirely enclosed by a second barrier, having a plurality of partially overlapping elastic layers. A needleless syringe is inserted through the plurality of partially overlapping elastic layers of the second barrier to introduce the hazardous materials into the container, and the second barrier prevents outflow of the hazardous materials upon extraction of the needleless syringe from the second aperture.

In another embodiment, the at least one port includes a third aperture, having a first mated-end enclosing the third aperture, where the first mated-end includes a unidirectional flow mechanism, and wherein the first mated-end connects to a second mated-end of the needleless syringe. The first mated-end securely introduces the hazardous materials into the container by connecting to the second mated-end of the needleless syringe, and the unidirectional flow mechanism prevents outflow of the hazardous materials from the first mated-end upon detachment of the needleless syringe.

In another embodiment, the at least one port includes a fourth aperture for introducing the hazardous materials into the container, a cylinder for isolating the hazardous materials introduced from the fourth aperture. The cylinder has an ingress opening and an egress opening, where the ingress opening aligns with the fourth aperture. The fourth port also includes an ingress cover positioned between the ingress opening of the cylinder and the fourth aperture to open and close the ingress opening, wherein the ingress cover moves in relation to the ingress opening, whereby allowing or preventing the introduction of the hazardous materials into the cylinder.

Furthermore, the fourth port includes an egress cover positioned below the egress opening of the cylinder to open and close the egress opening, wherein the egress cover moves in relation to the egress opening, whereby allowing or preventing the introduction of the hazardous materials from the cylinder to the container. The fourth port includes a rod, which connects the ingress cover and the egress cover, and simultaneously moves the ingress cover and the egress cover, through manipulation of a handle attached to the rod. Manipulation of the handle moves the ingress and egress covers so that the egress cover closes the egress opening when the ingress cover opens the ingress opening, and vice versa, whereby preventing direct access to the enclosed space of the container from the fourth aperture.

In another embodiment, the fourth aperture includes a fourth barrier, having the plurality of partially overlapping elastic layers, wherein the fourth aperture is entirely enclosed by the fourth barrier, whereby preventing outflow of the hazardous materials introduced into the cylinder.

In another embodiment, the device includes a pressure gauge in communication with at least a pressure indicator, located external to the container, where the pressure indicator shows a pressure level within the container.

In another embodiment, the device includes a pressure valve for releasing pressure within the container, wherein the pressure valve is connected to a filter having disinfecting properties. The pressure valve releases excess pressure from gases forming within the container, and the filter disinfects the gases released from the container through the pressure valve.

In another embodiment, the device includes an absorption gauge in communication with at least an absorption indicator, where the absorption indicator is located external to the container and shows a saturation level of the absorbent material within the container.

In another embodiment, the device includes a toxicity gauge in communication with at least a toxicity indicator located externally to the container, where the toxicity indicator shows the remaining effectiveness of the disinfecting properties of the disinfecting substance within the container.

In another embodiment, the device includes at least an attachment mechanism connected to at least an external surface of the container to connect at least a first container to a second container, to form a single separable unit.

In another embodiment, the device is combustible, and is constructed from at least a combustible material, so that the hazardous materials within the container can be incinerated without removing the hazardous materials from the container.

In another embodiment, the exterior surface of the container is at least one color.

In another embodiment, the device includes any and all of the embodiments of the at least one port described above, where all of the embodiments of the at least one port can be exclusive to the at least one chamber of the container.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention. In the drawings.

DETAILED DESCRIPTION OF EMBODIMENTS

Figure 1:
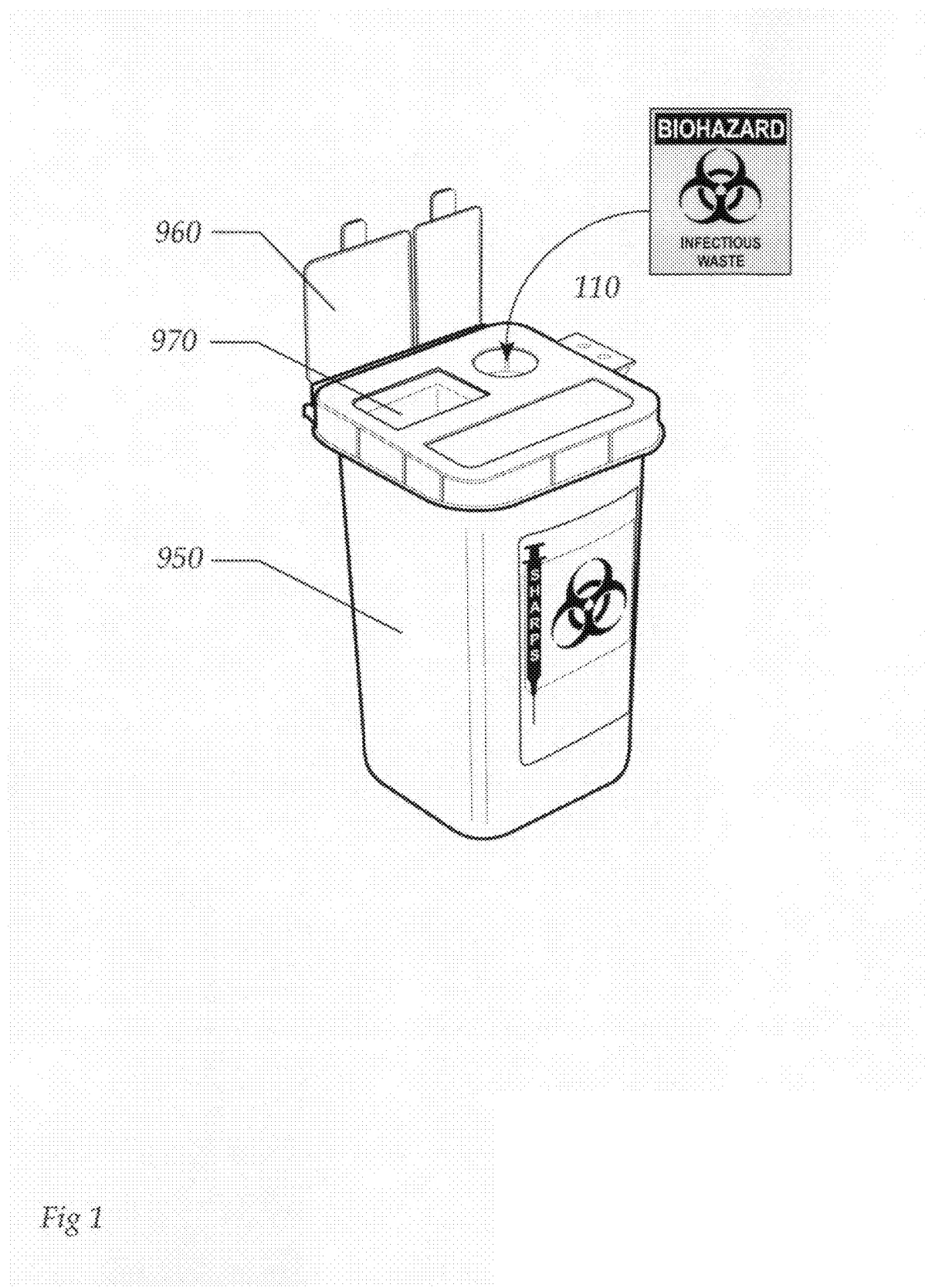
FIG. 1 is a side perspective view of a conventional Sharps™ container.

The accompanying drawings are described below, in which example embodiments in accordance with the present inventive concepts are shown. Specific structural and functional details disclosed herein are merely representative. This invention may be embodied in many alternate forms and should not be construed as limited to example embodiments set forth herein.

Accordingly, specific embodiments are shown by way of example in the drawings. It should be understood, however, that there is no intent to limit the invention to the particular forms disclosed, but on the contrary, the invention is to cover all modifications, equivalents, and alternatives falling within the spirit and scope of the claims.

It will be understood that, although the terms first, second, etc. are be used herein to describe various elements, these elements should not be limited by these terms. These terms are used to distinguish one element from another, but not to imply a required sequence of elements. For example, a first element can be termed a second element, and, similarly, a second element can be termed a first element, without departing from the scope of the present inventive concepts. As used herein, the term "and/or" includes any and all combinations of one or more of the associated listed items.

It will be understood that when an element is referred to as being "on," "connected to" "abutting," "coupled to," or "extending from" another element, it can be directly on, connected to, abutting, or coupled to the other element or intervening elements may be present. In contrast, when an element is referred to as being "directly on," "directly connected to," "directly abutting," "directly coupled to," or "directly extending from" another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

Conventional apparatus typically include cat litter or RedZ™ spill absorbent, where these ingredients are placed into the bottom of an empty and previously unused Sharps™ container. Any excess fluids, for example drugs, vaccines, blood, and so on, from needles or syringes are expelled into the container, and the used syringes and needles, as well as any other contaminated disposable medical instruments, are discarded in this same container for eventual disposal pertaining to proper procedures for the disposal of bio-hazardous materials. These fluids are left to drip and drain over the syringes and needles already placed in the container until a portion of the liquids find their way to the bottom of the container where the absorbing compound rests. Some portion of the dispensed or discarded fluids, which make it to the bottom of the container by way of gravity, are absorbed by the absorbing substance. However, a portion of the fluids remain attached to the outside walls of the container or on previously disposed needles and syringes as the dispensed liquid comes into contact with these objects after being expelled into the container. Although these fluids are absorbed, they are not disinfected and still pose a great risk of contamination. The fluids which happen do not come into contact with the absorbing material either remain on the untreated interior walls of the container or on other objects within the container, further increasing the risk of disease and contamination. These fluids are now a source of biohazardous contamination and are a possible cause of spreading disease. Even the fluids that are absorbed by the absorbent material within the container can be a source of contamination, a means for spreading infection and risk being released into the environment outside of the container. This can occur if the container is tipped or knocked over, which occurs frequently, or if the container is not emptied prior to the absorbing material reaching a saturation level.

The standard Sharps™ container is designed to store used or contaminated medical instrumentation, for example scalpels, syringes, knives, needles, and so on, and are therefore not generally designed to store liquids. Through the opening used to place objects into the container, both liquids not sequestered within the absorbing substance, which is typically just poured into the bottom of the Sharps™ container, as well as the absorbing substance containing the liquids can find their way out of the container and create a potential risk of contamination. The present usage of the Sharps™ container does not address the issue of securing or disinfecting contaminated fluids on most or all of the surfaces of container's interior surfaces, thereby promoting the risk of disease and contamination in what is expected to be a sterile environment.

In addition, disadvantages of present containment systems such as the Sharps™ containers and similar devices do not provide for (1) measuring or indicating the pressure level of gases accumulating within the system; (2) preventing contaminated gases from escaping from the system; (3) disinfecting contaminated gases released from the system; (4) measuring and indicating the saturation level of the absorbing material within the system; and (5) measuring or indicating the toxicity of the absorbent material within the system. While the common practice of using the Sharps' containers with an absorbent substance is an option to dispose of and store spent and non-reusable injectable fluids, bodily fluids, solid waste, gases, and so on, it is by no means secure and does not prevent the spread of infection or contamination, nor does it provide a means for measuring and indicating important system variables which are critical in maintaining a safe and sanitary medical environment.

In brief overview, embodiments of the present inventive concepts include a device that includes a secure depository where excess or contaminated fluids, typically introduced from or contained within some form of syringe, vial, or intravenous tubing can be deposited. The fluids are rendered unusable and stored in a secure storage container until properly disposed of. Syringes, needles, and other medical instruments commonly discarded after use can also be safely and securely deposited in the device to be disposed of later without risk of spreading disease or contamination. The present invention provides for a novel way to securely and safely deposit spent liquids, which may or may not be infectious, bio-hazardous or corrosive in nature into a secure storage receptacle. The absorbent substance secures any liquid within the container by absorbing it, and holding it within the absorbent substance, thereby securing it within the substance and preventing it from leaking or escaping.

Using various ports and apertures to introduce hazardous fluids, devices and materials into the container, the device allows vessels containing spent liquids to expel these liquids inside the internal boundaries of the system limiting or preventing spillage out of the vessel into the immediate environment. These vessels either fit into or connect into an aperture in the storage container, screw into position in such a way that the aperture of the vessel and the aperture of the port securely lock into place, or allow the vessel to penetrate the aperture, thus allowing a safe and secure introduction of hazardous materials into the container. These ports also have different interface mechanisms that allow for a one way introduction of hazardous materials into the container, so as to prevent the outflow so the hazardous materials once they have been introduced into the container.

Once a liquid is introduced into the system, it is realized that either through increases in volume into a closed space or through chemical reactions, pressure may increase or decrease within the system. The invention also contains a pressure valve to balance the pressure between the inside and outside of the system. Once the hazardous materials are deposited within the system, an absorbent material absorbs and disinfects the liquid hazardous materials. Once a satisfactory amount of liquid is sequestered within the system or the absorbent materials capability is exhausted, the entire container is disposed of with the contents securely enclosed inside.

Within the scope of this invention, such fluids are meant to include but are not limited to bodily fluids, pharmaceutical solutions, chemotherapeutic agents or intravenous solutions and preparations. These fluids would be deposited or placed inside the container which has a core or internal boundaries of the invention through the use of one or multiple openings allowing storage for proper disposal. These openings would be fitted with adaptable ports which provide a conduit from outside for placement of fluids into the system. Such fluids may be contained in but are not limited to syringes, intravenous tubing or bags, vials or other types of holding containers. The system includes an absorbent material that interacts with the liquids that deposited in one or multiple ways. The absorbent material can be a single material or a combination of multiple absorbent materials, and can be affixed to the interior surfaces of the container. The absorbent material can also be combined with a disinfecting substance to reduce or eliminate the chance of contamination or the spread of disease. The disinfecting substance can be a single substance or a combination of disinfecting substances, and can be affixed to the interior surfaces of the container, either independently or in combination with the absorbent material. Furthermore, the disinfecting substance and absorbent material can be included in an absorbent mesh layer which can be affixed to the interior surfaces of the container, where the interior surfaces of the container are any surfaces within the container, including partitions and enclosed chambers. This device also consists of attachment racks or clips to allow additional containers to be attached to the device. These additional containers may be specially designed to conform with stricter regulations, such as Resource Conservation and Recovery Act (RCRA) hazardous waste requirements, and may be removable from the device for more frequent disposal. The device many also be produced in any color to distinguish it based on purpose, location placement, and so on.

FIG. 1 shows a conventional Sharps™ container 950 including a disposal aperture 970 and an aperture lid 960. As is shown in FIG. 1, the only method that the conventional Sharps™ container 950 has of securing the disposal aperture 970 is a flip down aperture lid 960. The disposal aperture 970 is generally open and susceptible to outflow or spilling through the disposal aperture 970, or the uninhibited release of gases or contamination introduced into, or formed within the conventional container 950.

Figure 2:
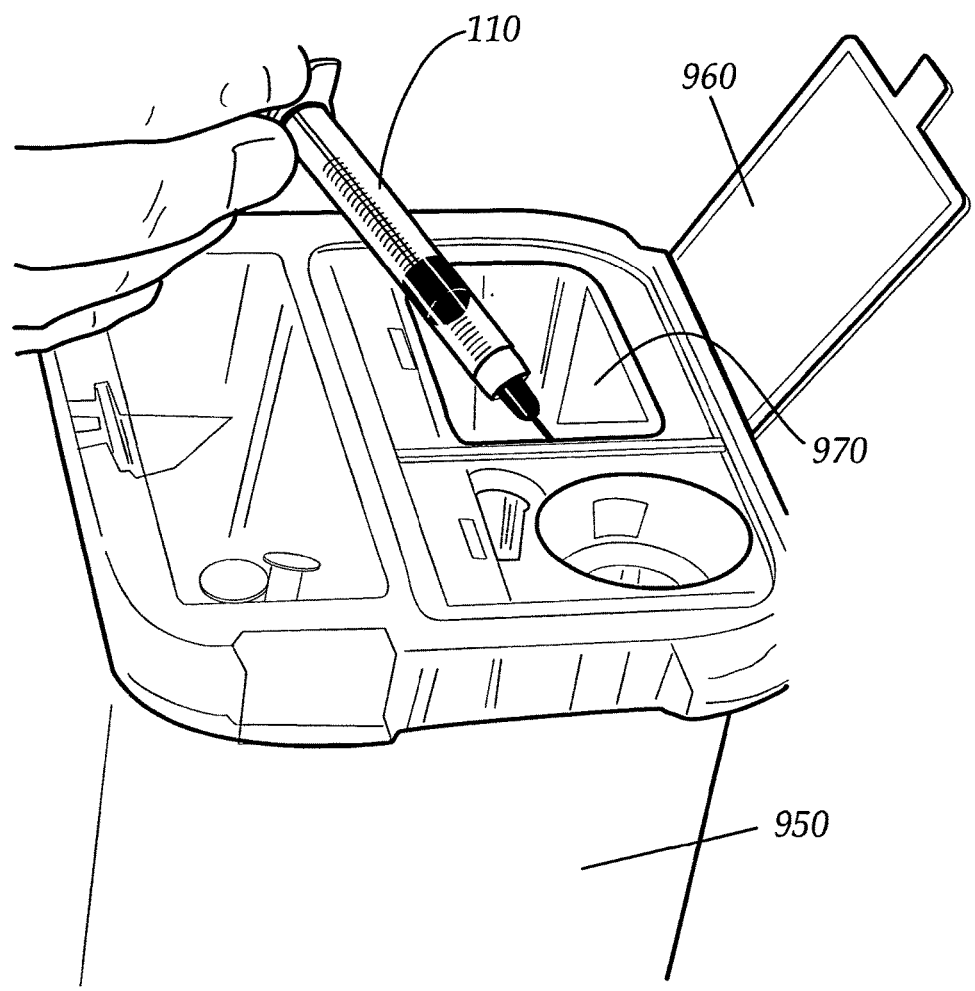
FIG. 2 is an angled top down perspective view of hazardous materials being introduced into a conventional Sharps™ container.

FIG. 2 shows the hazardous materials 110 being introduced into the conventional Sharps™ container 950 through the disposal aperture 970. The disposal aperture 970 is generally open and does not prevent the outflow of the hazardous materials 110 in the form of gases, and the aperture lid 960 does not prevent the accidental or intentional extraction of the hazardous materials 110 once introduced in the Sharps™ container 950. In addition, the hazardous materials 110 being introduced into the Sharps™ container 950 can aggregate on the interior walls, thereby eluding absorption by the RedZ™ or kitty litter typically loosely poured into the bottom of the conventional Sharps™ container 950.

Figure 3:
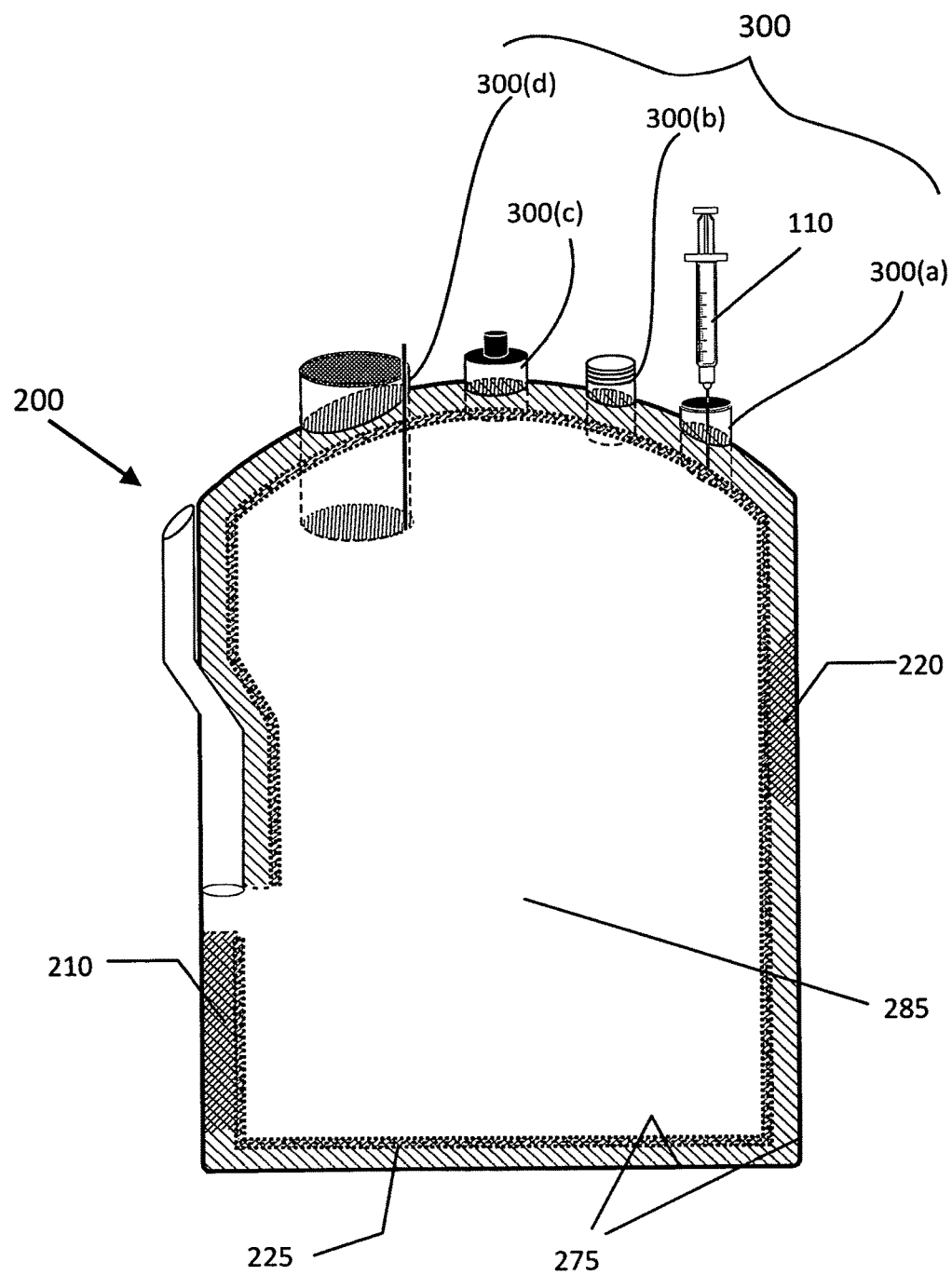
FIG. 3 is a cutaway perspective view of a device, in accordance with an embodiment.

FIG. 3 shows an embodiment of the described device including a container 200, having at least one interior surface 275 forming at least one chamber 285 within the container 200. The hazardous materials 110 are securely introduced into the at least one chamber 285 of the container 200 through at least one port 300, which can prevent outflow of the hazardous materials 110 once introduced into the container 200. An absorbent material 210 can be affixed to at least one interior surface 275 of the container 200, which can absorb the hazardous materials 110, thereby securing the hazardous materials 110 within the absorbent material 210 and preventing outflow of the hazardous materials 110 from the container 200. Once introduced into the container 200, a disinfecting substance 220, which can be affixed to the at least one interior surface 275 of the container 200, can disinfect the hazardous materials 110. The container 200 of FIG. 3 can facilitate the safe introduction of the hazardous materials 110 into the container 200 through the at least one port 300, which can prevent the outflow of the hazardous materials 110. The container 200 can also secure and disinfect the hazardous waste 110 coming into contact with the at least one interior surface 275 using the absorbent material 210 and the disinfecting substance 220, affixed to the at least one interior surface 275 of the container 200, thereby ensuring that all of the hazardous materials 110 introduced into the container 200 are secured and disinfected.

In another embodiment of the described device, an absorbent mesh layer 225 as shown in FIG. 3, having disinfecting properties, can also be affixed to the at least one interior surface 275 of the container 200 to secure and disinfect the hazardous materials 110. This container 200 secures and disinfects the hazardous waste 110 introduced into the container 200, thereby ensuring that all of the hazardous materials 110 introduced into the container 200 are secured and disinfected.

Figure 4:
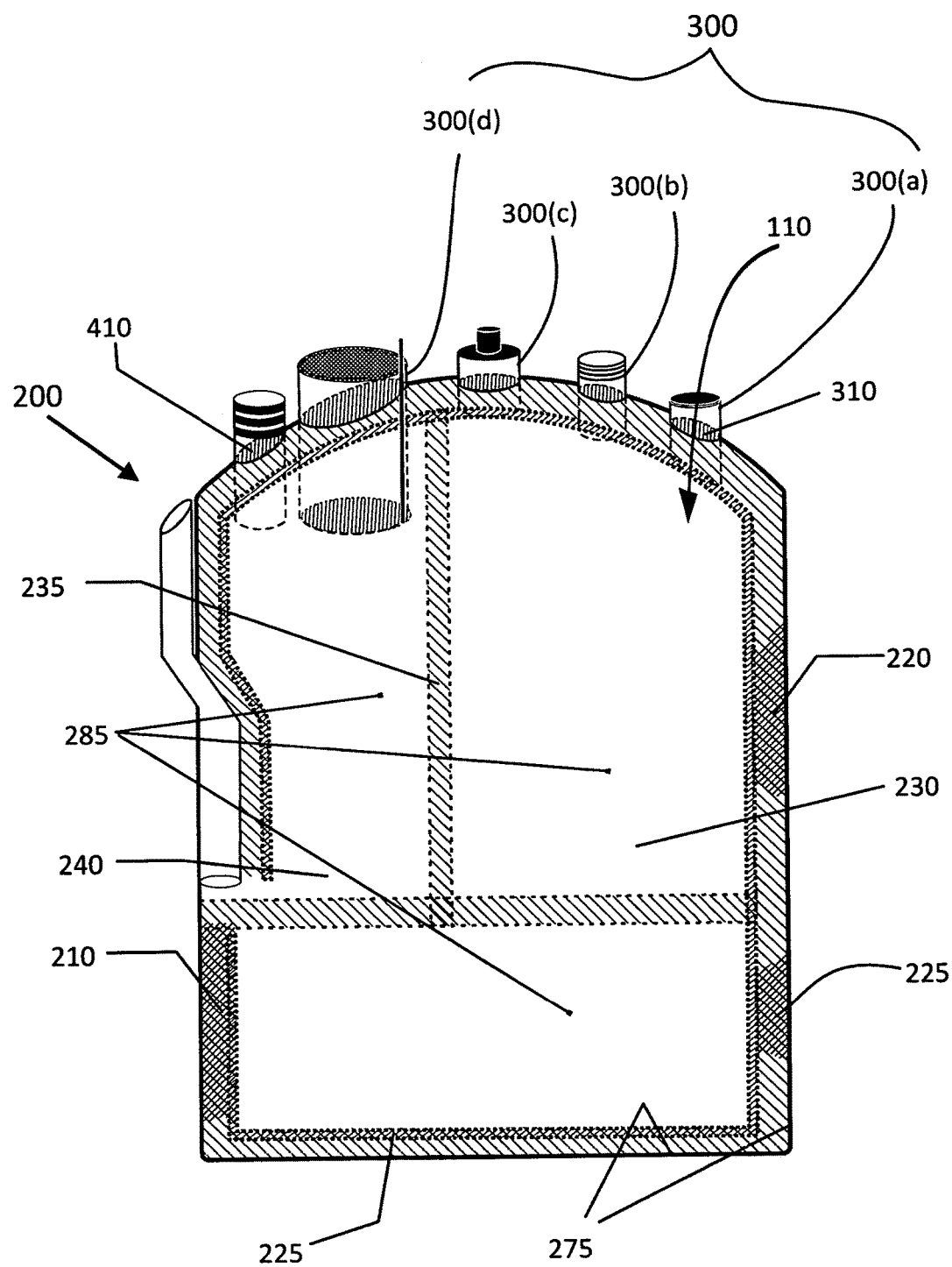
FIG. 4 is a cutaway perspective view of a port and respective aperture, in accordance with an embodiment.

FIG. 4 shows an embodiment of the described device, where the at least one chamber 285 of the container 200 is divided by a non-permeable partition 235 into at least a first chamber 230 and a second chamber 240. The first chamber 230 can include a first aperture 310 for introducing the hazardous materials 110 into the first chamber, and the second chamber 240 has at least a second aperture 410 for introducing the hazardous materials 110 into the second chamber 240. The absorbent material 210 and the disinfecting substance 220, or the absorbent mesh layer 225 can affix to the at least one interior surface 275 of the first chamber 230, the second chamber 240 and the non-permeable partition 235. The device described in FIG. 4 can introduce the hazardous materials 110 into separate chambers 230, 240 within the container 200 using the separate apertures 310, 410, where the separate apertures 310, 410 can separate the hazardous materials 110 introduced into the chambers 230, 240 according to physical characteristics. The absorbent material 210, the disinfecting substance 220, and the absorbent mesh layer 225 can be affixed to the at least one interior surface 275 of the chambers 230, 240 and the non-permeable partition 235, to secure and disinfect the hazardous waste 110.

Figure 5:
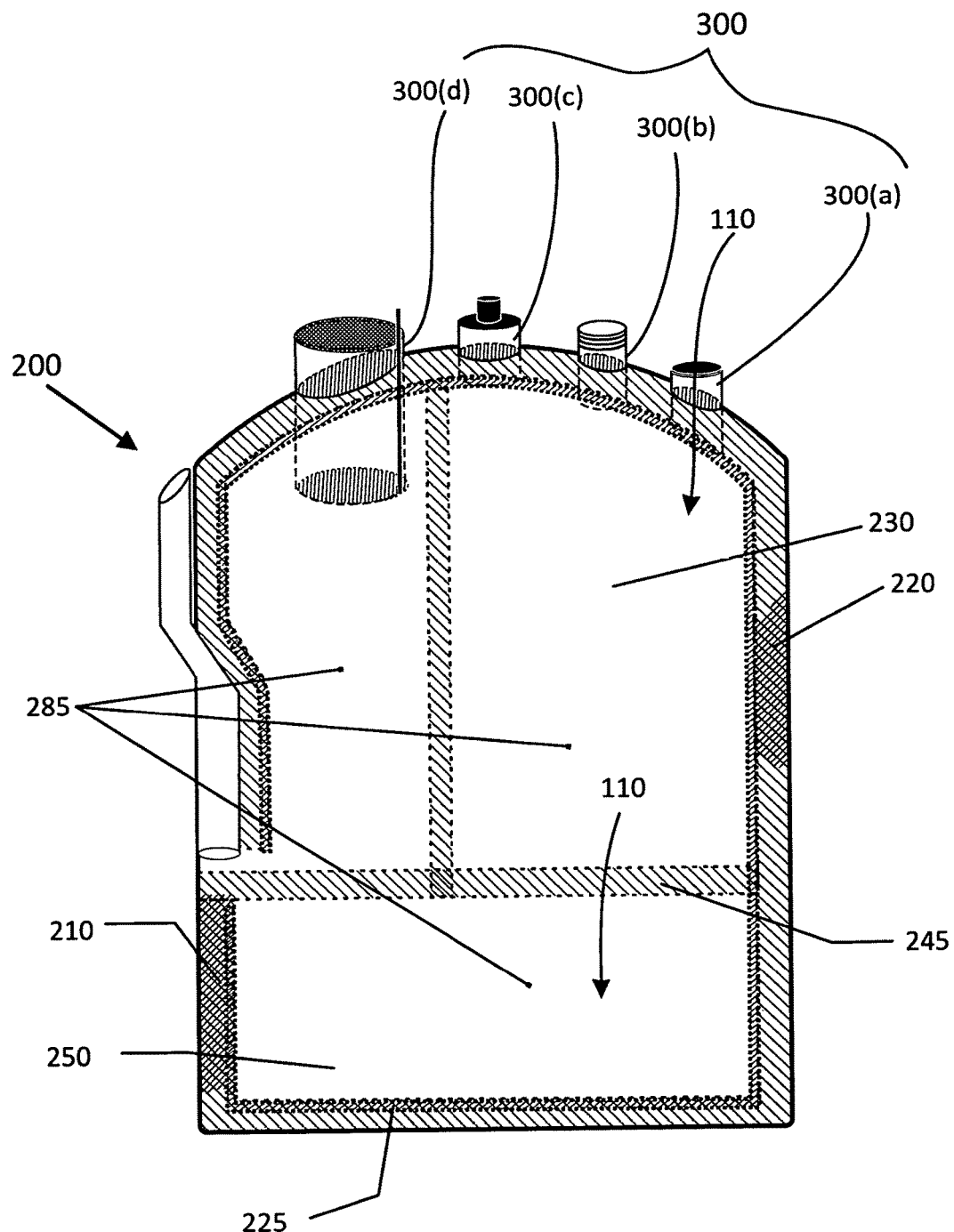
FIG. 5 is a cutaway perspective view of a port and respective aperture, in accordance with an embodiment.

FIG. 5 shows an embodiment of the described device, where a permeable partition 245 can divide the at least one chamber 285 of the container 200 into at least the first chamber 230 and a third chamber 250. The first chamber 230 has at least a first aperture 310 for the introduction of the hazardous materials 110 into the first chamber 230. The permeable partition 245 allows for at least partial transfer of the hazardous materials 110 from at least the first chamber 230 into the third chamber 250. The absorbent material 210 and the disinfecting substance 220, and the absorbent mesh layer 225 can be affixed to the at least one interior surface 275 of the first chamber 230, third chamber 250 and permeable partition 245. The device described in FIG. 5 can sort and filter the hazardous materials 110 introduced into at least the first chamber 230 by physical characteristics, depending upon the characteristics of the permeable partition 245. For example, the characteristics of the permeable partition 245 can allow the hazardous materials 110 in liquid form to transfer through to the third chamber 250, while preventing the hazardous materials 110 in solid form from transferring through to the third chamber 250.

Figure 6:
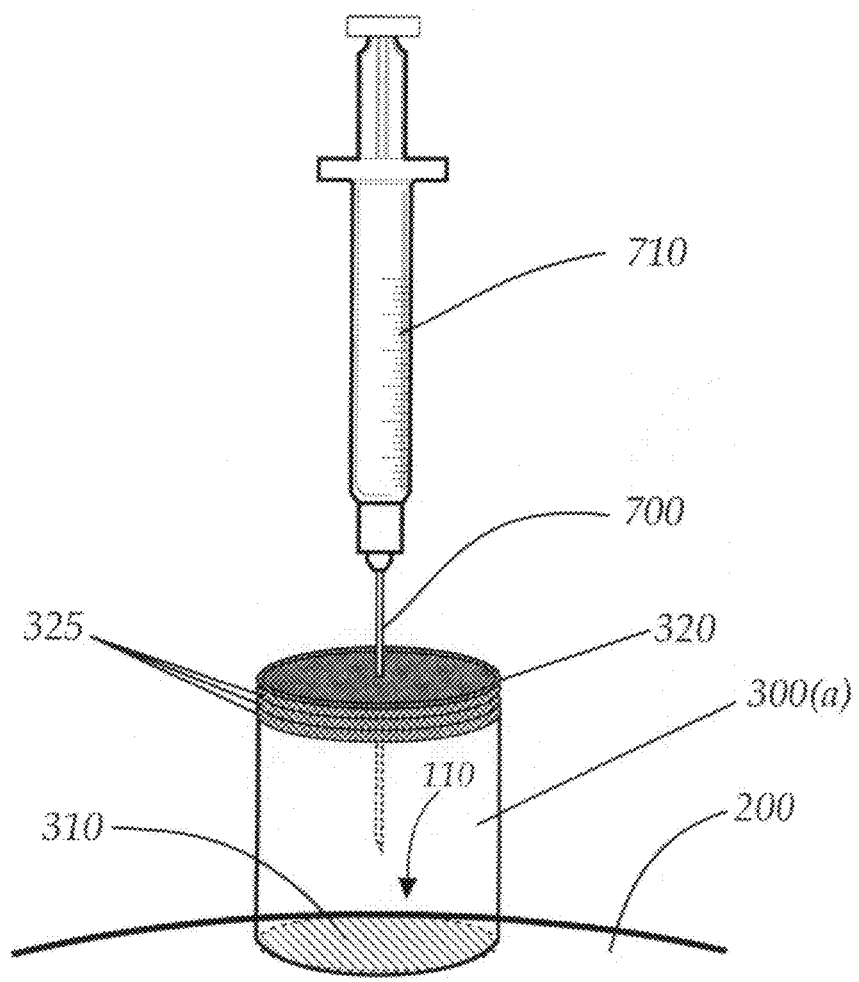
FIG. 6 is a cutaway perspective view of a port and respective aperture, in accordance with an embodiment.

FIG. 6 shows at least one port 300(a) in accordance with another embodiment. Here the at least one port 300(a) can include a first aperture 310 completely enclosed by a first barrier 320, having at least one elastic layer 325 stretched across the aperture 310. FIG. 6 also shows a needle 700, attached to a syringe 710, inserted through the at least one elastic layer 325 of the first barrier 320, to introduce the hazardous materials 110 through the first aperture 310 and into the container 200. When extracting the needle 700 from the first barrier 320, the at least one elastic layer 325 prevents the hazardous material 110 from escaping through the first aperture 310. The at least one port 300(a) described in FIG. 6 can prevent the hazardous materials 110 from escaping from at least the first aperture 310.

Figure 7:
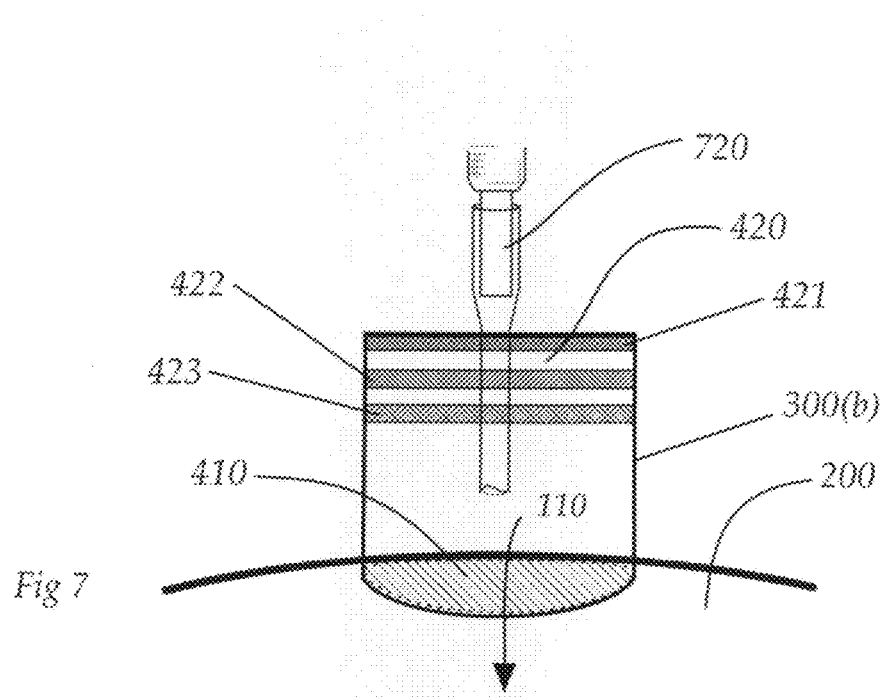
FIG. 7 is a cutaway perspective view of a port and respective aperture, in accordance with an embodiment.
Figure 7A:
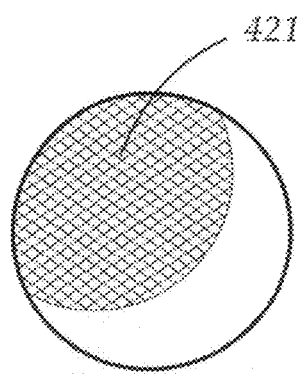
FIG. 7A is a top down perspective view of a port barrier shown in FIG. 7, in accordance with an embodiment.
Figure 7B:
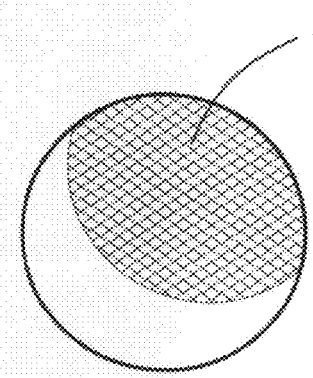
FIG. 7B is a top down perspective view of a port barrier shown in FIG. 7, in accordance with an embodiment.
Figure 7C:
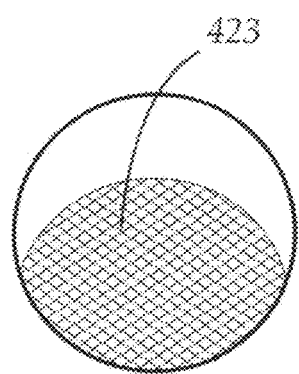
FIG. 7C is a top down perspective view of a port barrier shown in FIG. 7, in accordance with an embodiment.

FIG. 7 shows at least one port 300(b) in accordance with another embodiment. Here the at least one port 300(b) can include a second aperture 410 completely enclosed by a second barrier 420. The second barrier 420 can include at least a first elastic layer 421 at least partially covering the second aperture 410, a second elastic layer 422 at least partially covering the second aperture 410, and a third elastic layer 423 at least partially covering the second aperture 410.

FIGS. 7, 7A, 7B, 7C show the elastic layers 421, 422, 423 combined in offset alignment in relation to each other and layered in combination to form the second barrier 420, whereby the second barrier 420 can completely enclose the second aperture 410. FIG. 7 also shows a needleless syringe 720 inserted through the second barrier 420, for introducing the hazardous materials 110 through the second aperture 410 into the container 200. When extracting the needleless syringe 720 from the second barrier 420, the plurality of at least elastic layers 412, 422, 423 can prevent the hazardous material 110 from escaping through the second aperture 410. The at least one port 300(b) described in FIG. 7 can prevent the hazardous materials 110 from escaping from the second aperture 410.

Figure 8:
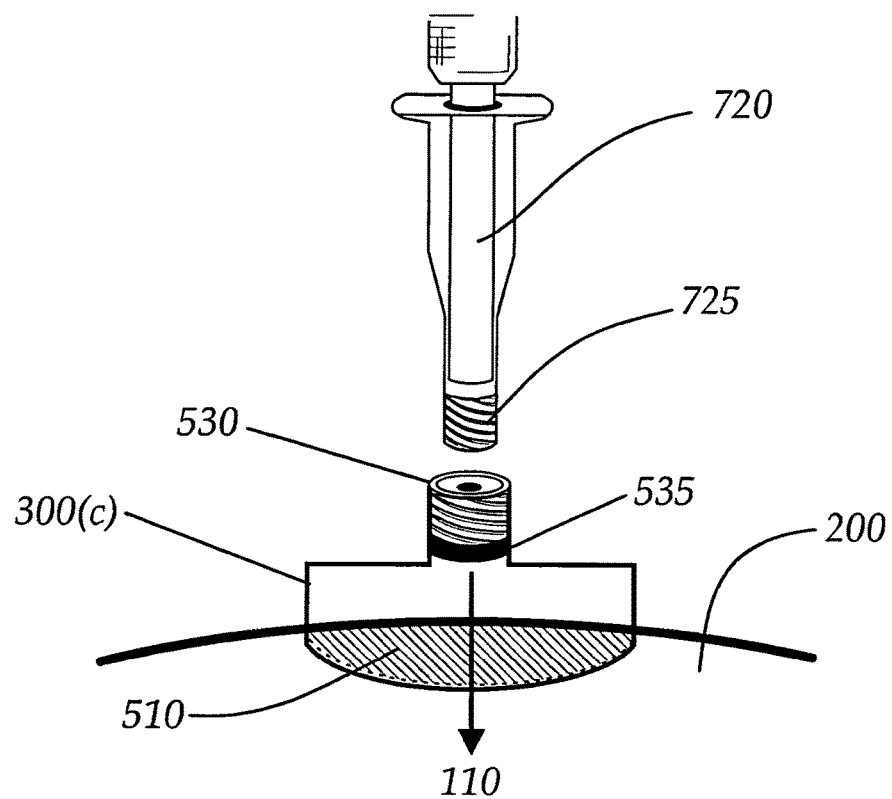
FIG. 8 is a cutaway perspective view of a port and respective aperture, in accordance with an embodiment.

FIG. 8 shows at least one port 300(c) in accordance with another embodiment. Here the at least one port 300(c) can include a third aperture 510 for introducing the hazardous materials 110 into the container 200. A first-mated end 530, having a unidirectional flow mechanism 535, can completely enclose the third aperture 510, and can connect with a second mated-end 725 of the needleless syringe 720. FIG. 8 shows the needleless syringe 720, having the second mated-end 725, connected to the first mated-end 530, for introducing the hazardous materials 110 through the third aperture 510 into the container 200. When disconnecting the second mated-end 725 from the first mated-end 530, the unidirectional flow mechanism 535 can prevent the hazardous material 110 from escaping through the third aperture 510. The at least port 300(c) described in FIG. 8 can prevent the hazardous materials 110 from escaping from the third aperture 510.

Figure 9:
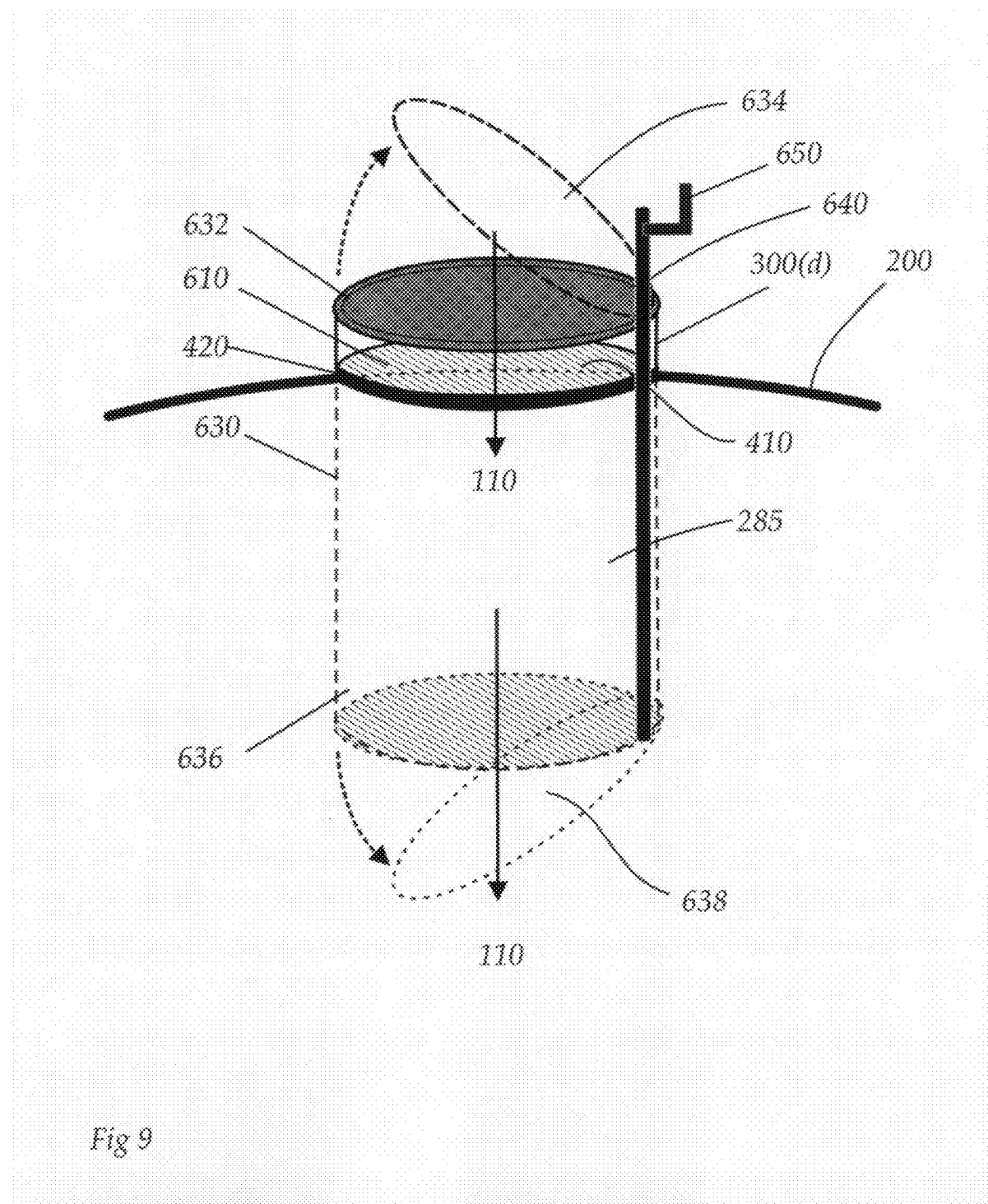
FIG. 9 is a cutaway perspective view of a port and respective aperture, in accordance with an embodiment.

FIG. 9 shows at least one port 300(d) in accordance with another embodiment. Here the at least one port 300(d) can include a fourth aperture 610 for introducing the hazardous materials 110 into a cylinder 630. The cylinder 630, vertically positioned within the container 200, can include an ingress opening 632 and an egress opening 636. The ingress opening 632 is aligned with the fourth aperture 610 for introducing the hazardous materials 110 into the cylinder 630, and the egress opening 636 opens into the container 200 for transferring the hazardous materials 110 from the cylinder 630 into the container 200. An ingress cover 634 for covering the ingress opening 632 can move in relation to the ingress opening 632 to open and close the ingress opening 632. An egress cover 638 for covering the egress opening 636 can move in relation to the egress opening 636 to open and close the egress opening 636. A rod 640, connected to the ingress cover 634 and the egress cover 638, can move the ingress cover 634 relative to the ingress opening 632, and can move the egress cover 638 relative to the egress opening 636. A handle 650 connected to the rod 640 can manipulate the rod 640 for moving the ingress cover 634 and egress cover 638. When the handle 650 is moved to a first position, the rod 640 moves the ingress cover 634 relative to the ingress opening 632 so as to uncover the ingress opening 632, whereby allowing the introduction of the hazardous materials 110 into the cylinder 630. Moving the ingress cover 634 so as to uncover the ingress opening 632 causes the rod 640 to close the egress cover 638 over the egress opening 636, whereby preventing the hazardous materials 110 in the cylinder 630 from being introduced into the container 200. When the handle 650 is moved to a second position, the rod 640 moves the ingress cover 634 relative to the ingress opening 632 so as to cover the ingress opening 632, whereby preventing the introduction of the hazardous materials 110 into the cylinder 630. Moving the ingress cover 634 so as to cover the ingress opening 632 causes the rod 640 to move the egress cover 638 so as to uncover the egress opening 636, whereby allowing the hazardous materials 110 from the cylinder 630 to be introduced into the container 200. The at least one port 300(d) described in FIG. 9 can prevent direct access to the at least one chamber 285 of the container 200, and it can prevent the hazardous materials 110 from escaping from the fourth aperture 610.

In accordance with another embodiment of the described device, the fourth aperture 610 can be in combination with the second barrier 420 having the second aperture 410, where the fourth aperture 610 and the second aperture 410 align, and the second barrier 420 encloses the fourth aperture 610. The second barrier 420 can include at least the first elastic layer 421 which at least partially covers the second aperture 410, the second elastic layer 422 which at least partially covers the second aperture 410, and the third elastic layer 423 which at least partially covers the second aperture 410. Combining the second barrier 420 with the fourth aperture 610 can prevent access to the hazardous materials 110 contained in the cylinder 630 while the ingress cover 634 is misaligned relative to the ingress opening 632.

Figure 10:
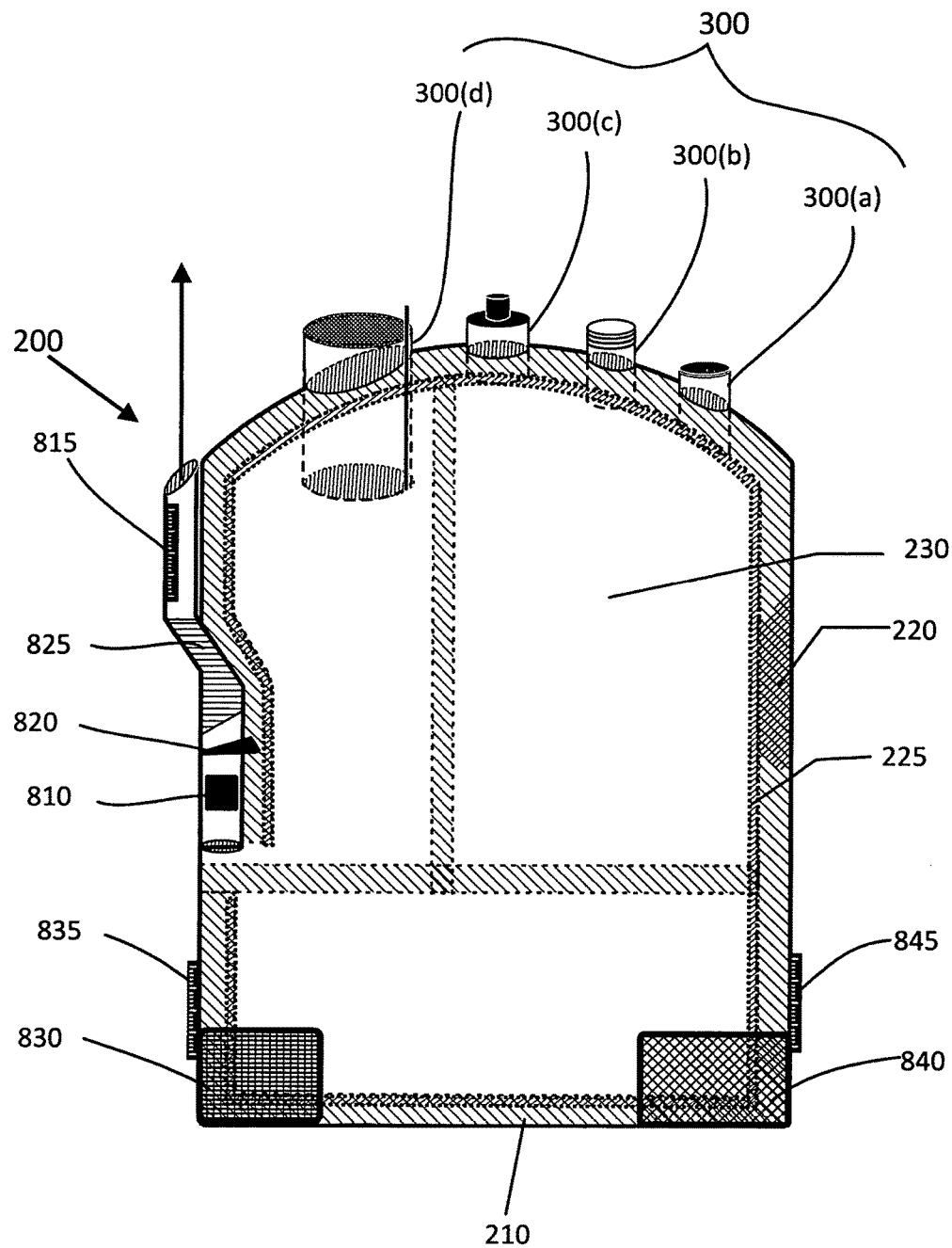
FIG. 10 is a cutaway perspective view of a device, in accordance with an embodiment.

In accordance with another embodiment of the described device as shown in FIG. 10, the device can include a pressure gauge 810 to measure a pressure level within the container 200 or within the at least one chamber 285. The pressure gauge 810 can be in communication with a pressure indicator 815, where the pressure indicator 815 shows the pressure level within the container 200, and is viewable from outside the container 200. This embodiment can measure and show the pressure level within the container 200.

In accordance with another embodiment of the described device, as shown in FIG. 10, the device can include a pressure valve 820 used to release pressure within the container 200. The pressure valve 820 is connected to a filter 825, having disinfecting properties, wherein the filter 825 filters and disinfects gases released from the container 200 through the pressure value 820. This embodiment can release pressure within the container 200, and filter and disinfect gases released from within the container 200.

In accordance with another embodiment of the described device, as shown in FIG. 10, the device can include an absorption gauge 830 to measure a saturation level of the absorbent material 210 or absorbent mesh layer 225 within the container 200. An absorption indicator 835, in communication with the absorption gauge 830, can show the saturation level of the absorbent material 210, and is viewable from outside the container 200. This embodiment can measure and show the saturation level of the absorbent material 210 or absorbent mesh layer 225 within the container 200.

In accordance with another embodiment of the described device, as shown in FIG. 10, the device can include a toxicity gauge 840 to measure a level of effectiveness of the disinfecting substance 220 or the absorbent mesh layer 225 within the container 200. The toxicity gauge 840 is in communication with a toxicity indicator 845, which shows the effectiveness level of the disinfecting substance 220 or the absorbent mesh layer 225, and which can be viewed from outside the container 200. This embodiment can measure and show the effectiveness level of the disinfecting substance 220 or the absorbent mesh layer 225 within the container 200.

In accordance with another embodiment of the described device, at least one external surface 255 of the container 200 can be at least a single color such as red, black, yellow, orange, green, and so on, for distinguishing the container 200 according to utility, purpose, location, and so on. The external surface 255 of the container 200 can also support printed messages such as "hazardous", "caution", or any other message.

In accordance with another embodiment of the described device, the container 200 is fabricated from at least a combustible material, which promotes the incineration of the container 200, so that the hazardous materials 110 within the container 200 can be incinerated without being removed from the container 200.

Figure 11:
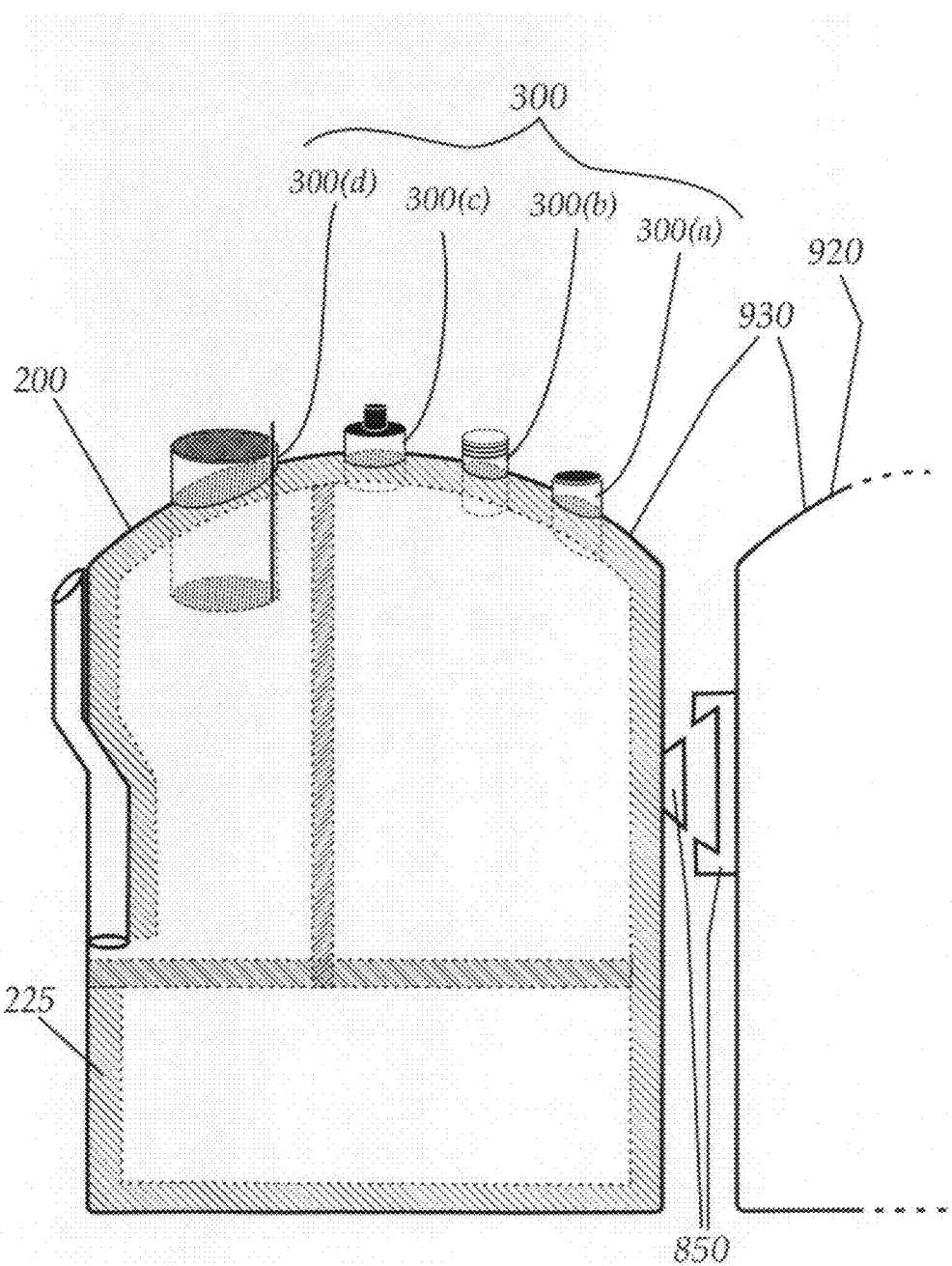
FIG. 11 is a cutaway perspective view of a device, in accordance with an embodiment.

In accordance with another embodiment of the described device as shown in FIG. 11, the device can include an attachment mechanism 850, which can include mechanisms, hooks, clamps, latches, clips, and so on, connected to the at least one exterior surface 255 of the container 200, for attaching at least a second container 920 to the at least one exterior surface 255 of the container 200. The attachment mechanism 850 can allow the container 200 and at least the second container 920 to be connected together into a single separable unit 930, for separately containing the hazardous materials 110 having different properties and different disposal requirements, such as RCRA hazardous waste requirements. Therefore, the containers 200, 920 can be connected together as the single separable unit 930 by the attachment mechanism 850, for convenience and safety, and can be separated for the individual disposal of the containers 200, 920 as needed or required.

Figure 12:
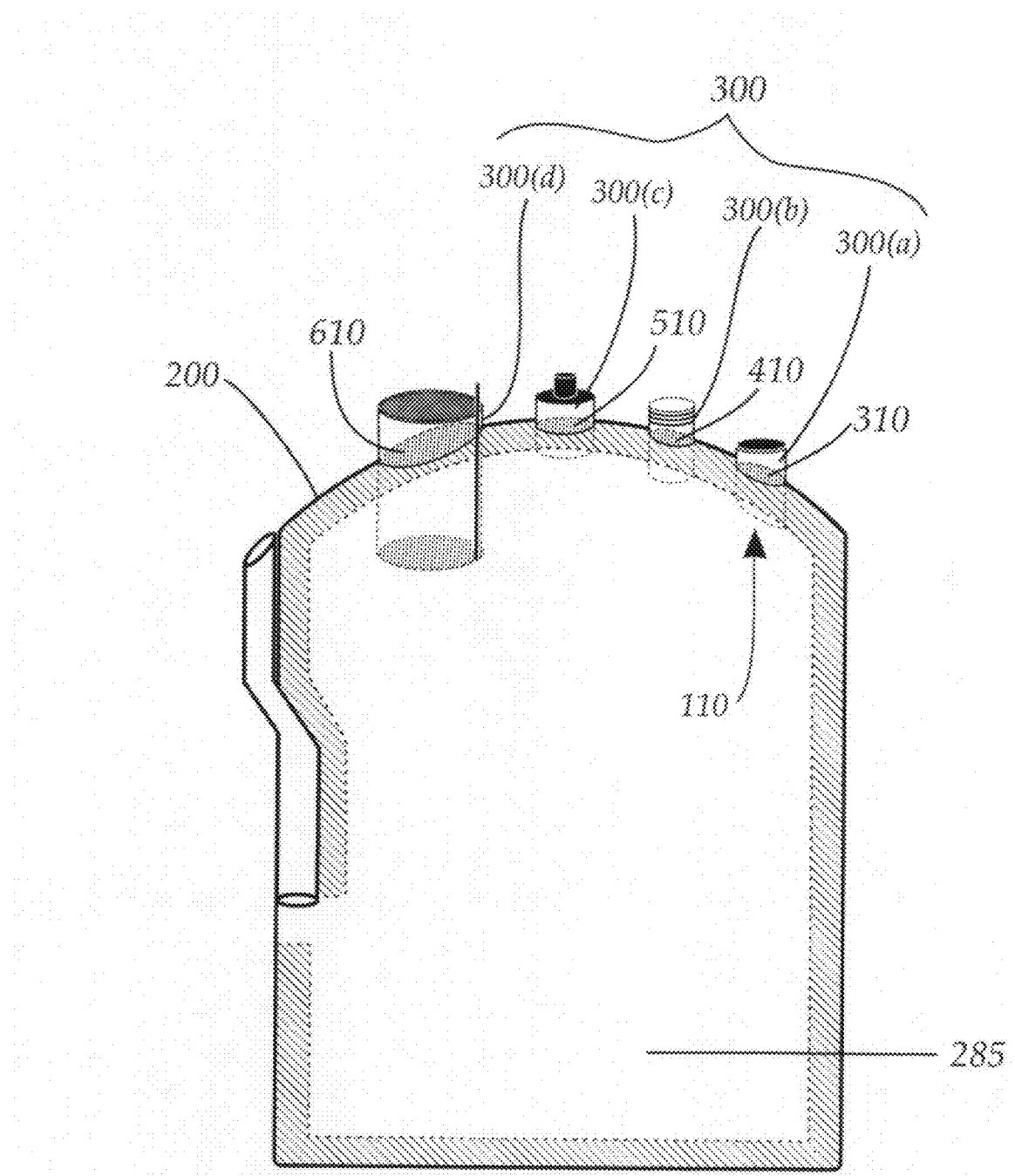
FIG. 12 is a cutaway perspective view of a device, in accordance with an embodiment.

In accordance with another embodiment of the described device as shown in FIG. 12, the device can include any one of the at least one port 300, all of the at least one port 300, or any combination of the at least one port 300 described in the above embodiments, wherein the at least port 300 can include the first aperture 310, second aperture 410, third aperture 510, and fourth aperture 610, whereby preventing direct access to the at least one chamber 285 of the container 200, and preventing outflow of the hazardous materials 110 from the container 200.

The foregoing inventive concepts may be embodied in many alternate forms and should not be construed as limited to example embodiments set forth herein. Accordingly, specific embodiments are shown by way of example in the drawings. It should be understood, however, that there is no intent to limit the invention to the particular forms disclosed, but on the contrary, the invention is to cover all modifications, equivalents, and alternatives falling within the spirit and scope of the claims.

What is claimed is:

1. A device for storing, securing and disinfecting hazardous materials introduced therein, the device comprising:
    a container having at least one interior surface, wherein the at least one interior surface forms at least one chamber within the container, for storing the hazardous materials introduced into the container;
    at least one port having an aperture and unidirectional access, for introducing the hazardous materials into the container and preventing outflow of the hazardous materials from the container;
    an absorbent material for securing the hazardous materials introduced into the container, wherein the absorbent material is affixed to the at least one interior surface of the container;
    a disinfecting substance for disinfecting the hazardous materials introduced into the container, wherein the disinfecting substance is affixed to the at least one interior surface of the container; and
    an absorbent mesh layer having disinfecting properties, for absorbing, securing and disinfecting the hazardous materials, wherein the absorbent mesh layer is affixed to the at least one interior surface of the container.

2. The device of claim 1 wherein the absorbent material is combined with the disinfecting substance, for securing and disinfecting the hazardous materials introduced into the container.

3. The device of claim 1, wherein the at least one chamber comprises:
    a first chamber for storing the hazardous materials;
    a second chamber for storing the hazardous materials; and
    a non-permeable partition for separating the at least one chamber into the first chamber and the second chamber, whereby the hazardous materials stored in the first chamber are separate from the hazardous materials stored in the second chamber.

4. The device of claim 3, wherein the at least one chamber further comprises:
a third chamber for storing the hazardous materials; and
a permeable partition for separating the at least one chamber into the first chamber and the third chamber, whereby the hazardous materials introduced into the first chamber pass at least partially through the permeable partition into the third chamber.

5. The device of claim 3, wherein the first chamber is completely separate from at least the second chamber, and wherein the at least one port is exclusive to the first chamber, for the exclusive introduction of the hazardous materials into the first chamber.

6. The device of claim 1, wherein the at least one port comprises:
a first aperture for introducing the hazardous materials into the container; and
a first barrier for the unidirectional introduction of the hazardous materials into the container using a needle attached to a syringe, having at least one elastic layer completely enclosing the first aperture, wherein the needle penetrates the first barrier, whereby introducing the hazardous materials into the container and preventing outflow of the hazardous materials once the needle is extracted from the first barrier.

7. The device of claim 1, wherein the at least one port comprises:
a second aperture for introducing the hazardous materials into the container; and
a second barrier for the unidirectional introduction of the hazardous materials into the container using a needleless syringe, having a plurality of partially overlapping elastic layers, wherein the second barrier completely encloses the second aperture, whereby preventing outflow of the hazardous materials once the needleless syringe is extracted from the second barrier.

8. The device of claim 7, wherein the second barrier comprises:
a first elastic layer for at least partially enclosing the second aperture;
a second elastic layer for at least partially enclosing the second aperture, in combination with and misaligned in relation to the first elastic layer; and
a third elastic layer at least partially enclosing the second aperture, in combination with and misaligned in relation to the first elastic layer and the second elastic layer, wherein the plurality of partially overlapping elastic layers completely encloses the second aperture, whereby preventing the outflow of the hazardous materials once the needleless syringe is extracted from the second barrier.

9. The device of claim 1, wherein the at least one port comprises:
a third aperture for introducing the hazardous materials into the container;
a first mated-end completely enclosing the third aperture, for connecting to a second mated-end of a needleless syringe; and
a unidirectional flow mechanism connected to the first mated-end, for preventing the outflow of the hazardous materials through the first mated-end upon detachment of the second mated-end of the needleless syringe.

10. The device of claim 1, wherein the at least one port comprises:
a fourth aperture for introducing the hazardous materials into the container;
a cylinder for isolating the hazardous materials introduced from the fourth aperture, wherein the cylinder comprises:
an ingress opening aligned with the fourth aperture, for passing the hazardous materials from the fourth aperture into the cylinder;
an egress opening for passing the hazardous materials from the cylinder to the container;
an ingress cover covering the ingress opening, for opening and closing the ingress opening, whereby allowing or preventing the hazardous materials to pass into the cylinder;
an egress cover covering the egress opening, for opening and closing the egress opening, whereby allowing or preventing the hazardous materials to pass from the cylinder to the container;
a rod connecting the ingress cover and the egress cover, for moving the ingress cover and the egress cover, wherein the egress cover closes the egress opening when the ingress cover is lifted, whereby enabling the hazardous materials to be introduced into the cylinder while preventing the hazardous materials from being introduced into the container, and where the egress cover opens the egress opening when the ingress cover is closed, whereby enabling the hazardous materials to be introduced into the container while preventing the hazardous materials from being introduced into the cylinder; and
a handle connected to the rod, for moving the ingress cover and the egress cover.

11. The device of claim 10, wherein the at least one port further comprising:
a fourth barrier having a plurality of partially overlapping elastic layers enclosing the fourth aperture, for allowing the introduction of the hazardous materials and preventing outflow of the hazardous materials into the cylinder.

12. The device of claim 1 further comprising:
a pressure gauge for measuring a pressure level within the container; and
a pressure indicator in communication with the pressure gauge, for indicating the pressure level within the container.

13. The device of claim 1 further comprising:
a pressure valve for releasing pressure within the container; and
a filter having disinfecting properties and connected to the pressure valve, for disinfecting gas released from the container through the pressure valve.

14. The device of claim 1 further comprising:
an absorption gauge for measuring a saturation level of the absorbent material; and
an absorption indicator in communication with the absorption gauge, for indicating a saturation level of the absorbent material in the container.

15. The device of claim 1 further comprising:
a toxicity gauge for measuring a level of effectiveness of the disinfecting substance; and
a toxicity indicator in communication with the toxicity gauge, for indicating the effectiveness of the disinfecting properties of the disinfecting substance within the container.

16. The device of claim 1 further comprising:
an attachment mechanism connected to an external surface of the container, wherein the attachment mechanism connects at least a first container and a second container, for forming a single separable unit.

17. The device of claim 1, wherein the device is constructed of at least a combustible material, for incinerating the container.

18. The device of claim 1, wherein an exterior surface of the container is at least one color, for indicating a specific utility or purpose.

19. The device of claim 1, wherein the at least one port comprises:

a first port comprising:

a first aperture for introducing the hazardous materials into the container; and a first barrier for the unidirectional introduction of the hazardous materials into the container using a needle attached to a syringe, having at least one elastic layer completely enclosing the first aperture, wherein the needle penetrates the first barrier, whereby introducing the hazardous materials into the container and preventing outflow of the hazardous materials once the needle is extracted from the first barrier;

a second port comprising:

a second aperture for introducing the hazardous materials into the container; and a second barrier for the unidirectional introduction of the hazardous materials into the container using a needleless syringe, having a plurality of partially overlapping elastic layers, wherein the second barrier completely encloses the second aperture, whereby preventing outflow of the hazardous materials once the needleless syringe is extracted from the second barrier;

a third port comprising:

a third aperture for introducing the hazardous materials into the container;

a first mated-end completely enclosing the third aperture, for connecting to a second mated-end of the needleless syringe; and a unidirectional flow mechanism connected to the first mated-end, for preventing the outflow of the hazardous materials through the first mated-end upon detachment of the second mated-end of the needleless syringe; and a fourth port comprising:

a fourth aperture having an additional plurality of partially overlapping elastic layers enclosing the fourth aperture for introducing the hazardous materials into the container;

a cylinder for isolating the hazardous materials introduced from the fourth aperture, wherein the cylinder comprises:

an ingress opening aligned with the fourth aperture, for passing the hazardous materials from the fourth aperture into the cylinder;

an egress opening for passing the hazardous materials from the cylinder to the container;

an ingress cover positioned between the ingress opening and the fourth aperture, for opening and closing the ingress opening, wherein the ingress cover moves in relation to the ingress opening, whereby allowing or preventing the hazardous materials to pass into the cylinder;

an egress cover positioned below the egress opening, for opening and closing the egress opening, wherein the egress cover moves in relation to the egress opening, whereby allowing or preventing the hazardous materials to pass from the cylinder to the container;

a rod connecting the ingress cover and the egress cover, for simultaneously moving the ingress cover and the egress cover, wherein the egress cover closes the egress opening when the ingress cover opens the ingress opening, and where the egress cover opens the egress opening when the ingress cover closed the ingress opening, whereby the ingress opening is open when the egress opening is closed, and the ingress opening is closed when the egress opening is open; and a handle connected to the rod, for moving the ingress cover and the egress cover.

\* \* \* \* \*